US00PP09824P

United States Patent [19]

VandenBerg

[11] Patent Number: Plant 9,824

[45] Date of Patent: Mar. 11, 1997

[54] CHRYSANTHEMUM PLANT NAMED 'BRONZE PAPILLON'

[75] Inventor: Cornelis P. VandenBerg, Salinas, Calif.

[73] Assignee: Yoder Brothers, Inc., Barberton, Ohio

[21] Appl. No.: 525,299

[22] Filed: Sep. 7, 1995

[51] Int. Cl.[6] ..... A01H 5/00

[52] U.S. Cl. ..... Plt./82.3

[58] Field of Search ..... Plt./74.1, 82.4, Plt./82.5

[56] References Cited

U.S. PATENT DOCUMENTS

| | | | |
|---|---|---|---|
| P.P. 7,435 | 1/1991 | VandenBerg | Plt./74.1 |
| P.P. 8,549 | 1/1994 | VandenBerg | Plt./82.4 |
| 4,616,099 | 10/1986 | Sparkes | 47/58 |

OTHER PUBLICATIONS

Broertjes, et al., 1980, "A mutant of a mutant of a . . . Irradiation of progressive radiation–induced mutants in a mutation breeding programme with *Chrysanthemum* morifolium", Euphytica, 29:525–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by x–rays", Am. Soc. Hort Sci. Proc., pp. 613–620.

Broertjes, 1966, "Mutation breeding of chrysanthemums", Euphytica, 15:156–162.

Dowrick, et al., 1966, "The induction of mutations in chrysanthemum using x– and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Bronze Papillon particularly characterized by its flat capitulum form; flat capitulum form; daisy capitulum type; greyed-red ray floret color; diameter across face of capitulum of 35 to 37 mm when fully opened, when grown as a pinched spray pot mum; very floriferous, with an excellent display of many small flowers; photoperiodic flowering response to short days of 52 to 62 days; plant height, with 14 long days after sticking unrooted cuttings and with 1 to 2 applications of 2500 ppm B-9 SP, ranges from 20 to 28 cm when grown as a pinched pot mum with 4 cuttings in a 15 cm pot; branching pattern is spreading and very prolific, with each plant developing 6 to 8 laterals after pinch; and recommended as a spray pot mum.

1 Drawing Sheet

The present invention comprises a new and distinct cultivar of Chrysanthemum, botanically known as *Dendranthema grandiflora,* and referred to by the cultivar name Bronze Papillon.

Bronze Papillon, identified as 6959 (93-#02001) is a spontaneous mutation of the cultivar Papillon, disclosed in U.S. Plant Pat. No. 7,435, and was selected to expend the color range of the parental variety. Bronze Papillon was discovered and selected under the directive of Cornelis P. VandenBerg as one flowering plant within a flowering block of Papillon in October of 1992, in a controlled environment in Pendleton, S.C.

The first act of asexual reproduction of Bronze Papillon was accomplished when vegetative cuttings were taken from the initial selection in January of 1993 in a controlled environment in Pendleton, S.C., by technicians working under the directive of Cornelis P. VandenBerg.

Horticultural examination of controlled flowerings of successive plantings has shown that the unique combination of characteristics as herein disclosed for Bronze Papillon are firmly fixed and are retained through successive generations of asexual reproduction.

Bronze Papillon has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Bronze Papillon, which, in combination, distinguish this Chrysanthemum as a new and distinct cultivar:

1. Flat capitulum form.
2. Daisy capitulum type.
3. Greyed-red ray floret color.
4. Diameter across face of capitulum of 35 to 37 mm when fully opened, when grown as a pinched spray pot mum.
5. Very floriferous, with an excellent display of many small flowers.
6. Photoperiodic flowering response to short days of 52 to 62 days.
7. Plant height, with 14 long days after sticking unrooted cuttings and with 1 to 2 applications of 2500 ppm B-9 SP, ranges from 20 to 28 cm when grown as a pinched pot mum with 4 cuttings in a 15 cm pot.
8. Branching pattern is spreading and very prolific, with each plant developing 6 to 8 laterals after pinch.
9. Recommended as a spray pot mum.

The accompanying photographic drawing is a side view of a potted mum of Bronze Papillon, with 4 cuttings in a 15 cm pot, with the colors being as nearly true as possible with illustrations of this type.

Of the commercial cultivars known to the inventor, the most similar in comparison to Bronze Papillon is the parent cultivar Papillon. All traits of Bronze Papillon are similar to those of Papillon, except for the ray floret color. The ray floret color of Bronze Papillon is greyed-red (R.H.S. 179B to 179C, overcast with 39C), while the ray floret color of Papillon is described as red-purple (R.H.S. 71B to 71C).

The new cultivar can also be compared to sibling cultivar Pink Papillon, also a spontaneous mutation and disclosed in pending Ser. No. 08/525,314, and sibling cultivar Cherry Papillon, an induced mutation of Papillon disclosed in U.S. Plant Pat. No. 8,549. All siblings differ from each other and from the parent by ray floret color. Cherry Papillon further differs from its parent and from the other siblings by the relatively faster color fading of the ray florets.

In the following description color references are made to the Royal Horticultural Society Colour Chart. The color values were determined on plant material grown as a pinched spray pot mum in Salinas, Calif. on Jan. 30, 1995.

Classification:

*Botanical.*—*Dendranthema grandiflora* cv Bronze Papillon.

*Commercial.*—Flat daisy spray pot mum.

INFLORESCENCE

A. Capitulum:

*Form.*—Flat.

*Type.*—Daisy.

*Diameter across face.*—35 to 37 mm when fully opened.

B. Corolla of ray florets: Color designations or values are for flowers which have just fully opened.

*Color (general tonality from a distance of three meters).*—Greyed-red.

*Color (upper surface).*—179B to 179C, overcast with 39C.

*Color (under surface).*—181D.

*Shape.*—Straight, oblong, slightly ribbed.

C. Corolla of disc florets:

*Color (mature).*—12A.

*Color (immature).*—3A with slight overcase of 144C.

D. Reproductive organs:

*Androecium.*—Present on disc florets only; moderate pollen.

*Gynoecium.*—Present on both ray and disc florets.

PLANT

A. General appearance:

*Height.*—20 to 28 cm when grown as a pinched pot mum with 14 long days after sticking unrooted cuttings prior to start of short days, with 1 to 2 applications of 2500 ppm B-9 SP.

*Branching pattern.*—Spreading and very prolific.

B. Foliage:

*Color (Upper surface).*—147A.

*Color (under surface).*—147B.

*Shape.*—Small, lobed and slightly serrated.

What is claimed is:

1. A new and distinct Chrysanthemum plant named Bronze Papillon, as described and illustrated.

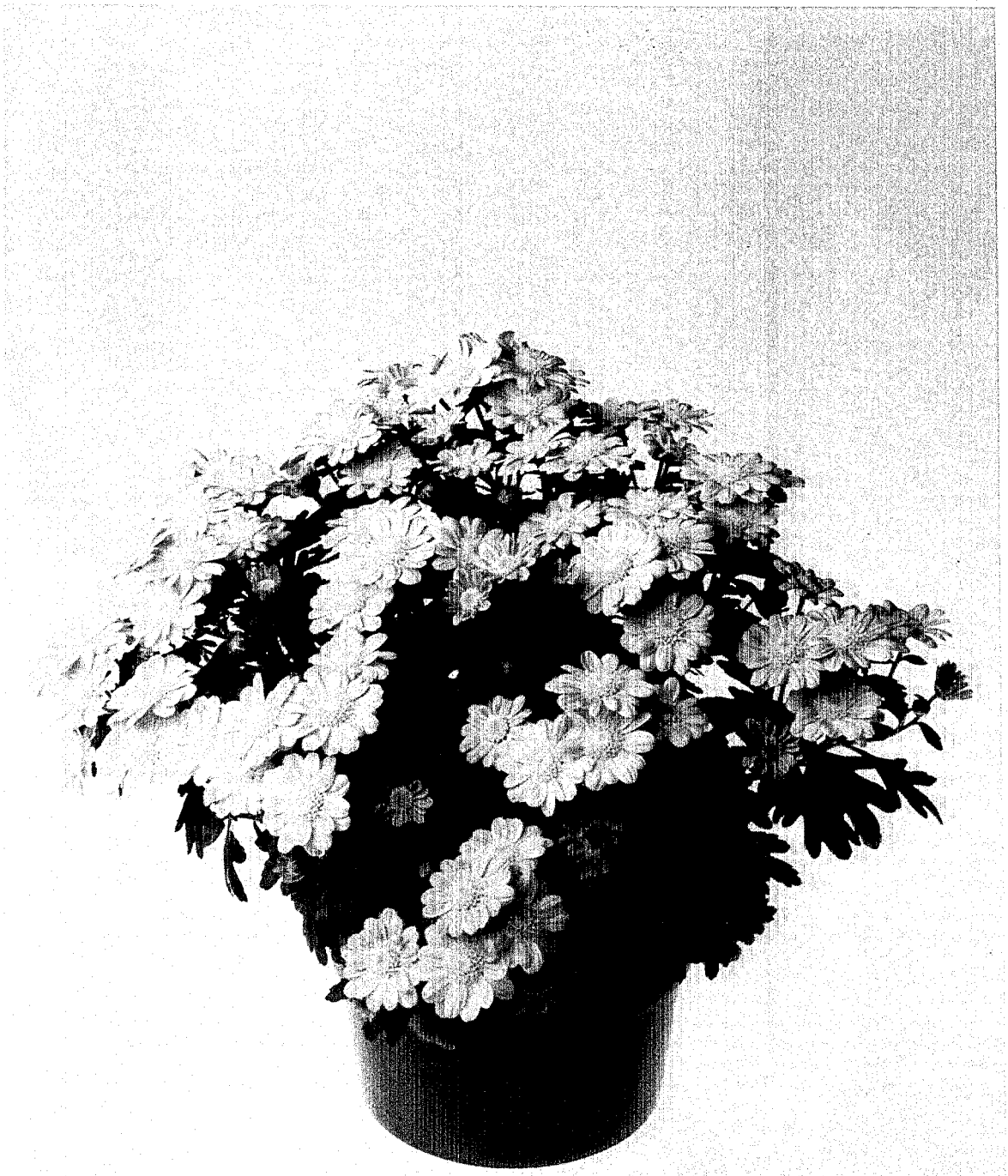

* * * * *